(12) United States Patent
Maass Sepúlved et al.

(10) Patent No.: US 8,927,246 B2
(45) Date of Patent: Jan. 6, 2015

(54) **METHOD TO INCREASE THE PRODUCTION OF EXTRACELLULAR POLYMERIC SUBSTANCES (EPS) IN A *ACIDITHIOBACILLUS FERROOXIDANS* CULTURE BY THE INHIBITION OF ENZYMES OF TRICARBOXILIC ACID CYCLE**

(75) Inventors: Alejandro Eduardo Maass Sepúlved, Santiago (CL); Pablo Andrés Moreno Cortéz, Santiago (CL); Marko Antonio Budinich Abarca, Santiago (CL); Pilar Angélica Parada Valdecantos, Colina (CL); Leandro Mauricio Padilla Iglesias, Colina (CL); Marlen Nayibe Barreto Roa, Colina (CL)

(73) Assignees: Universidad de Chile (CL); BioSigma S.A. (CL)

( * ) Notice: Subject to any disclaimer, the term of this patent is extended or adjusted under 35 U.S.C. 154(b) by 467 days.

(21) Appl. No.: 13/035,336

(22) Filed: Feb. 25, 2011

(65) Prior Publication Data

US 2011/0212527 A1    Sep. 1, 2011

(30) Foreign Application Priority Data

Mar. 1, 2010  (CL) .................................... 178-2010

(51) Int. Cl.
*C12N 9/99* (2006.01)
*C12P 1/04* (2006.01)
*C12N 1/38* (2006.01)
*C12P 19/04* (2006.01)

(52) U.S. Cl.
CPC ... *C12N 1/38* (2013.01); *C12P 1/04* (2013.01); *C12P 19/04* (2013.01)
USPC ............................ 435/184; 435/244; 435/170

(58) Field of Classification Search
None
See application file for complete search history.

(56) References Cited

U.S. PATENT DOCUMENTS 7,127,379 B2  10/2006  Palsson et al.

OTHER PUBLICATIONS

T. Gehrke et al. "Importance of Extracellular Polymeric Substances from *Thiobacillus ferrooxidans* for Bioleaching", Applied and Environmental Micriobiology 64(7):2743-2747. (1998).*
Bayer et al. "Evidence from inhibitor studies for conformational changes of citrate synthase." *Eur J Biochem* vol. 120 (1) (1981) pp. 155-160.
Boquist et al. "Inhibition by alloxan of mitochondrial aconitase and other enzymes associated with the citric acid cycle." *FEBS Letters* vol. 178 (2) (1984) pp. 245-248.
Dhariwal et al. "NADP-specific isocitrate dehydrogenase of *Mycobacterium phlei* ATCC 354: purification and characterization." *J Gen Microbiol* vol. 133 (9) (1987) pp. 2457-2460.
Else et al. "A new spectrophotometric assay for citrate synthase and its use to assess the inhibitory effects of palmitoyl thioesters." *Biochem J* vol. 251 (3) (1988) pp. 803-807.
Kim et al. *Bacterial Physiology and Metabolism, chapter 12*, Cambridge University Press, 2008 p. 460.
Llaneras and Picó, J. Biosci. Bioeng. (2008) 105(1):1-11).
Morrison et al. "Biochemistry of fluoroacetate poisoning: the effect of fluorocitrate on purified aconitase." *Biochem J* vol. 58 (3) (1954) pp. 473-479.
Salvarrey et al. "Citrate synthase from *Crithidia fasciculata*: inhibition by adenine nucleotides and suramin." *Comp Biochem Physiol, B* vol. 72 (1) (1982) pp. 165-168.
Schwartz et al. "alpha-Fluoro acid and alpha-fluoro amide analogs of acetyl-CoA as inhibitors of citrate synthase: effect of pKa matching on binding affinity and hydrogen bond length." *Biochemistry* vol. 34 (47) (1995) pp. 15459-15466.
Shin et al. "Anti-diabetic effects of DA-11004, a synthetic IDPc inhibitor in high fat high sucrose diet-fed C57BL/6J mice." *Arch Pharm Res* vol. 27 (1) (2004) pp. 48-52.
Tórtora et al. "Mitochondrial aconitase reaction with nitric oxide, S-nitrosoglutathione, and peroxynitrite: mechanisms and relative contributions to aconitase inactivation." *Free Radic Biol Med* vol. 42 (7) (2007) pp. 1075-1088.
Watling. "The bioleaching of sulphide minerals with emphasis on copper sulphides—A review." *Hydrometallurgy* vol. 84 (1-2) (2006) pp. 81-108.
Yang et al. "Inactivation of NADP(+)-dependent isocitrate de-hydrogenase by nitric oxide." *Free Radic Biol Med* vol. 33 (7) (2002) pp. 927-937.
Yoshino et al. Inhibition by aluminum ion of NAD- and NADP-dependent isocitrate dehydrogenases from yeast. Int J Biochem (1992) vol. 24 (10) pp. 1615-1618.
Zanatta et al. "In vitro evidence that D-serine disturbs the citric acid cycle through inhibition of citrate synthase activity in rat cerebral cortex." *Brain Research* vol. 1298 (2009) pp. 186-193.
Barreto et al. "Identification of a Gene Cluster for the Formation of Extracellular Polysaccharide Precursors in the Chemolithoautotroph Acidithiobacillus ferrooxidans." *Applied & Enviro. Microbiol*. vol. 71. No. 6. 2005. pp. 2902-2909.
Gehrke et al. "Importance of Extracellular Polymeric Substances from Thiobacillus ferrooxidans for Bioleaching."*Applied & Environ. Microbiol*. vol. 64. No. 7. 1998. pp. 2743-2747.
Rawlings. "Characteristics and adaptability of iron-and sulfur-oxidizing microorganisms used for the recovery of metals from minerals and their concentrates." *Microbial Cell Factories*. vol. 4. No. 13. 2005. pp. 1-15.
Sand et al. "Extracellular polymeric substances mediate bioleaching/ biocorrosion via interfacial processes involving iron(III) ions and acidophilic bacteria." *Research in Microbiol*. vol. 157. 2006. pp. 49-56.

* cited by examiner

*Primary Examiner* — Rebecca Prouty
(74) *Attorney, Agent, or Firm* — Merchant & Gould P.C.

(57) ABSTRACT

A method of increasing the production of extracellular polymeric substances (EPS) in an *Acidithiobacillus ferrooxidans* culture is disclosed. The method includes inhibiting an enzyme, such as citrate synthase, aconitase, or isocitrate dehydrogenase, in the tricarboxylic acid (TCA) cycle leading to alpha-ketoglutarate.

4 Claims, 2 Drawing Sheets

METHOD TO INCREASE THE PRODUCTION OF EXTRACELLULAR POLYMERIC SUBSTANCES (EPS) IN A *ACIDITHIOBACILLUS FERROOXIDANS* CULTURE BY THE INHIBITION OF ENZYMES OF TRICARBOXILIC ACID CYCLE

This application claims benefit of Serial No. 178-2010, filed 1 Mar. 2010 in Chile and which application is incorporated herein by reference. To the extent appropriate, a claim of priority is made to the above disclosed application.

FIELD OF INVENTION

The present invention is relevant in biomining, particularly in bioleaching. A method to increase the production of extracellular polymeric substances (EPS) in a *Acidithiobacillus ferrooxidans* culture, one of the most important microorganisms in biomining, is presented. This method has been developed using a mathematical model of *Acidithiobacillus ferrooxidans* metabolism, which allows to predict how to enhance EPS production, that was validated experimentally, giving origin to the method of the invention. EPS is responsible for bacterial adhesion to the mineral and biofilm formation and are therefore of great importance in bioleaching.

BACKGROUND OF THE INVENTION

Biomining can be defined as the use of microorganisms in the recovery of metals from minerals. Its traditional expression is bioleaching, the solubilization of metals from the corresponding sulfide minerals in an acidic medium using the direct or indirect action of microorganisms (Rawlings D. E., MicrobCell Fact. 4(1) (2005) 13).

For example, species from the *Acidithiobacillus* genre are capable of oxidizing reduced sulfur compounds, such as sulfide, elemental sulfur, thionates, etc. using oxygen as an electron acceptor, which allows the solubilization of metallic ions from minerals. During this process species such as sulfite and thiosulfate are generated as intermediates and sulfuric acid is generated as a final product.

Within the variety of microorganisms that participate in these processes, one of the most studied is *Acidithiobacillus ferrooxidans*, an acidophilic, autotrophic and quimiolitotrophic bacteria, which means that it lives in environments with acidic pH between 1,3 and 4, it uses $CO_2$ as carbon source and it obtains energy from inorganic compounds. In particular, *Acidithiobacillus ferrooxidans* oxidizes iron (II) to iron (III) using oxygen as an electron acceptor. Iron (III) is a potent oxidizing agent, that can oxidize reduced sulfur compounds or other reduced compounds (Watling. The bioleaching of sulphide minerals with emphasis on copper sulphides—A review. Hydrometallurgy (2006) vol. 84 (1-2) pp. 81-108).

The usual practice of bioleaching processes in the mining industry consists in charging the mineral previously crushed on an impermeable carpet forming "piles", which are later irrigated with a diluted solution of sulfuric acid. The solubilized metal in the percolated solution that elutes from the pile (known as Pregnant Leaching Solution or PLS) is then recuperated in successive stages of extraction by solvent and electrodeposition.

Since bioleaching is a microbiological process, its efficiency can be improved by inoculating the mineral with leaching microorganisms. This inoculation can take place when the mineral is charged or during the irrigation of the pile. In the vicinity of bioleaching piles it is possible to install and operate bioreactors for the production of such microorganisms (Morales P., Badilla, R. 2006. "Proceso para aumentar la velocidad de biolixiviación de minerales o concentrados de especies metálicas sulfuradas que comprende inocular continuamente solución de lixiviación que contiene microorganismos aislados de tipo *Acidithiobacillus thiooxidans* o en conjunto con microorganismos aislados de tipo *Acidithiobacillus ferrooxidans*". Solicitud de Patente Chilena N°2006-02911).

It has been described that extracellular polymeric substances (EPS) from *Acidithiobacillus ferrooxidans*, responsible for bacterial adhesion to the mineral and biofilm formation are crucial for bioleaching. It has been demonstrated that pirite bioleaching by *Acidithiobacillus ferrooxidans* is significantly greater in bacteria activated with EPS that in those without it (T. Gehrke et al, Appl. Environ. Microbiol. 64 (1998) p. 2743-2747). EPS seems to have 2 roles in bioleaching: (i) mediate bacterial adhesion to the sulfide mineral surface, and (ii) concentrate iron (III) ions in the mineral-microorganism interface by complexation with uronic acids or other EPS residues, allowing the oxidative attack on the sulfur to take place. (Sand W., Gehrke T., Research in Microbiology 157 (2006)49-56).

Having established the importance of EPS in bioleaching, the problem is how to increase EPS production in leaching microorganisms like *Acidithiobacillus ferrooxidans*. Although the identification of genes involved in EPS formation in *Acidithiobacillus ferrooxidans* has been accomplished (Barreto et al., Appl. Environ. Microbiol. 71 (2005) 2902-2909), methods to improve its EPS production have not yet been developed.

The present invention tackles the problem of generating microbial cultures that carry metabolic compounds or products that improve the bioleaching rate, proposing a strategy that assures biomass production together with EPS generation or accumulation, hence obtaining a biomass culture with enhanced characteristics, more efficient for bioleaching. The technical problem has been analyzed from a metabolic engineering point of view, developing a mathematical model that represents *Acidithiobacillus ferrooxidans*' metabolism, based on the genome annotation of *Acidithiobacillus ferrooxidans* strain Wenelen (Sugio T., Miura A., Parada P., Badilla R. (2005), Cepa bacteriana de *Acidithiobacillus ferrooxidans* denominada Wenelen, Patent number CL 44546). Simulations developed using the model made possible the determination of which metabolic pathways must be intervene in order to increase EPS specific productivity in *Acidithiobacillus ferrooxidans* Wenelen.

SUMMARY OF INVENTION

A mathematical model of *Acidithiobacillus ferrooxidans* metabolism has been developed. The objective of the model was to predict which metabolic pathways involved in EPS biosynthesis can be favored in order to increase EPS production in culture, aiming to improve bioleaching properties.

Model analysis showed that tricarboxylic acid cycle pathway (TCA) plays a key role in biomass production and is uncoupled with EPS synthesis. It should be pointed that any metabolic pathway can be described by acid compounds as well as their salt forms.

As result of a series of simulations performed using this model, it was concluded that if TCA can be blocked, it would diminish the growth rate and increase significantly the EPS in the existing biomass.

To implement such strategy, it was determined that the inhibition of any enzyme of the TCA cycle leading to alpha-ketoglutarate, without affecting oxalacetate production, according to FIG. 1, can be used. Particularly, citrate synthase, aconitase and isocitrate dehydrogenase. For the present invention, any kind of inhibition method can be used, being the more popular, but not limited to, genetic manipulation and addition of chemical substances, which inhibit each particular enzyme.

Genetic manipulation consists in altering the genomic material in such a way that metabolic network will be modified and properties of microorganisms changes (Palsson B. O. and Edwards J., Method for the evolutionary design of biochemical reaction networks, U.S. Pat. No. 7,127,379). In the present invention, such modification will correspond with manipulate genes producing the aforementioned enzymes, in a way that they were less chemically active.

A second way to limit the activity is using some chemical substance, which binds materially to the structure of the enzyme (Hong Kim B. and Gadd G. M., Bacterial Physiology and Metabolism, chapter 12, page 460, Cambridge University Press, 2008). Table 1 shows a list, based in a literature survey, of known inhibitors for the mentioned enzymes.

TABLE 1

List of known inhibitors for the mentioned enzymes of TCA.

| Enzyme | Inhibitor | Reference |
|---|---|---|
| Isocitrate dehidrogenase | aluminium | Yoshino et al. Inhibition by aluminum ion of NAD- and NADP-dependent isocitrate dehydrogenases from yeast. Int J Biochem (1992) vol. 24 (10) pp. 1615-8 |
| | oxalomalate | Dhariwal y Venkitasubramanian. NADP-specific isocitrate dehydrogenase of *Mycobacterium phlei* ATCC 354: purification and characterization. J Gen Microbiol (1987) vol. 133 (9) pp. 2457-60 |
| | p-cloromercuribenzoate | Dhariwal y Venkitasubramanian. NADP-specific isocitrate dehydrogenase of *Mycobacterium phlei* ATCC 354: purification and characterization. J Gen Microbiol (1987) vol. 133 (9) pp. 2457-60 |
| | DA-11004 | Shin et al. Anti-diabetic effects of DA-11004, a synthetic IDPc inhibitor in high fat high sucrose diet-fed C57BL/6J mice. Arch Pharm Res (2004) vol. 27 (1) pp. 48-52 |
| | nitric oxide | Yang et al. Inactivation of NADP(+)-dependent isocitrate dehydrogenase by nitric oxide. Free Radic Biol Med (2002) vol. 33 (7) pp. 927-37 |
| citrate synthase | palmitoyl - CoA | Else et al. A new spectrophotometric assay for citrate synthase and its use to assess the inhibitory effects of palmitoyl thioesters. Biochem J (1988) vol. 251 (3) pp. 803-7 |
| | palmitoyl tioglicolato | Else et al. A new spectrophotometric assay for citrate synthase and its use to assess the inhibitory effects of palmitoyl thioesters. Biochem J (1988) vol. 251 (3) pp. 803-7 |
| | (3R,S)-3,4-Dicarboxi-3-hidroxibutil-CoA | Bayer et al. Evidence from inhibitor studies for conformational changes of citrate synthase. Eur J Biochem (1981) vol. 120 (1) pp. 155-60 |
| | FCMX | Schwartz et al. alpha-Fluoro acid and alpha-fluoro amide analogs of acetyl-CoA as inhibitors of citrate synthase: effect of pKa matching on binding affinity and hydrogen bond length. Biochemistry (1995) vol. 34 (47) pp. 15459-66 |
| | FAMX | Schwartz et al. alpha-Fluoro acid and alpha-fluoro amide analogs of acetyl-CoA as inhibitors of citrate synthase: effect of pKa matching on binding affinity and hydrogen bond length. Biochemistry (1995) vol. 34 (47) pp. 15459-66 |

TABLE 1-continued

List of known inhibitors for the mentioned enzymes of TCA.

| Enzyme | Inhibitor | Reference |
|---|---|---|
| | D-Serine | Zanatta et al. In vitro evidence that D-serine disturbs the citric acid cycle through inhibition of citrate synthase activity in rat cerebral cortex. Brain Research (2009) vol. 1298 pp. 186-93 |
| | suramin | Salvarrey y Cazzulo. Citrate synthase from *Crithidia fasciculata*: inhibition by adenine nucleotides and suramin. Comp Biochem Physiol, B (1982) vol. 72 (1) pp. 165-8 |
| | ATP | Salvarrey y Cazzulo. Citrate synthase from *Crithidia fasciculata*: inhibition by adenine nucleotides and suramin. Comp Biochem Physiol, B (1982) vol. 72 (1) pp. 165-8 |
| aconitase | fluoroisocitrate | Morrison y Peters. Biochemistry of fluoroacetate poisoning: the effect of fluorocitrate on purified aconitase. Biochem J (1954) vol. 58 (3) pp. 473-9 |
| | alloxan | Boquist y Ericsson. Inhibition by alloxan of mitochondrial aconitase and other enzymes associated with the citric acid cycle. FEBS Letters (1984) vol. 178 (2) pp. 245-8 |
| | nitric oxide | Tórtora et al. Mitochondrial aconitase reaction with nitric oxide, S-nitrosoglutathione, and peroxy nitrite: mechanisms and relative contributions to aconitase inactivation. Free Radic Biol Med (2007) vol. 42 (7) pp. 1075-88 |
| | S-nitrosoglutation | Tórtora et al. Mitochondrial aconitase reaction with nitric oxide, S-nitrosoglutathione, and peroxynitrite: mechanisms and relative contributions to aconitase inactivation. Free Radic Biol Med (2007) vol. 42 (7) pp. 1075-88 |
| | peroxinitrite | Tórtora et al. Mitochondrial aconitase reaction with nitric oxide, S-nitrosoglutathione, and peroxynitrite: mechanisms and relative contributions to aconitase inactivation. Free Radic Biol Med (2007) vol. 42 (7) pp. 1075-88 |

In particular, a preferred implementation but not limiting of the present invention is the block of TCA cycle by selective inhibition of aconitasa enzyme (EC 4.4.1.3), which catalyzes the citrate to isocitrate conversion.

Another particular but not limiting realization of the present invention is limiting aconitase specifically by the fluoroisocitrate anion. From this point on, we will identify fluoroisocitrate o any of their salt forms as FIC.

This method allows an increase of 30% in specific productivity of *A. ferroxidans* Wenelen.

DETAILED DESCRIPTION OF THE INVENTION

Figure 1:
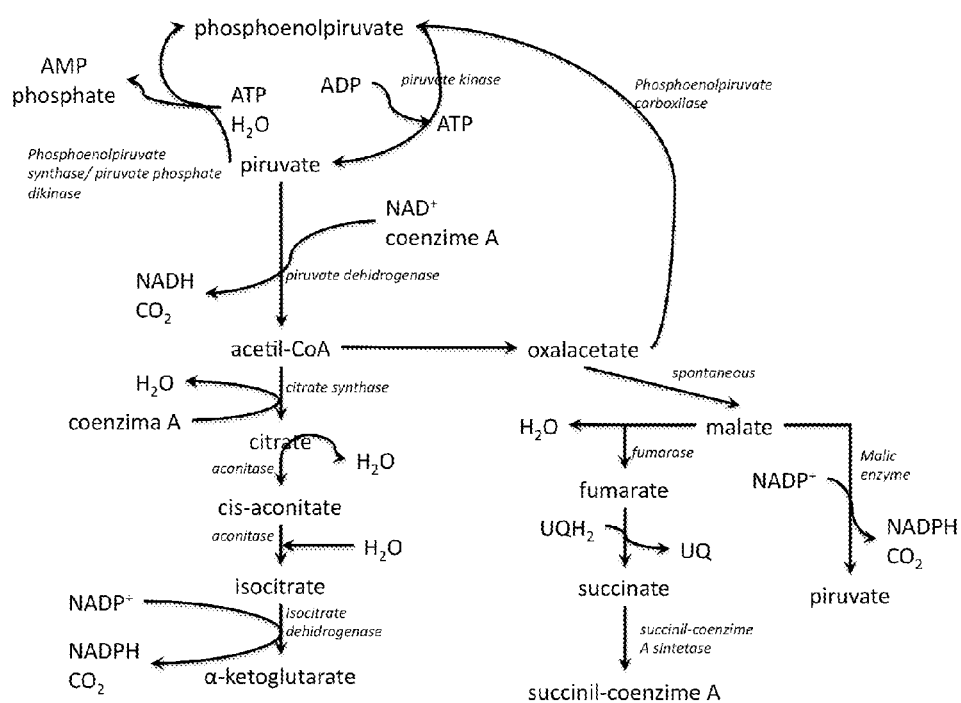
FIG. 1: *Acidithiobacillus ferrooxidans* Wenelen metabolic pathways relevant to the invention. Any of the paths characterized by the step from acetyl-CoA to a-ketoglutarate are susceptible of being used according to the method of invention.

A mathematical model of *Acidithiobacillus ferrooxidans* Wenelen (Sugio T., Miura A., Parada P., Badilla R., 2005, Cepa bacteriana de *Acidithiobacillus ferrooxidans* denominada Wenelen, Patente number CL 44546) has been developed aiming to establish strategies to increase the carbon flux in EPS production metabolic pathways, in order to obtain an EPS rich culture, and therefore a more efficient one for bioleaching.

To develop this model, *Acidithiobacillus ferrooxidans* Wenelen metabolic network was established. A metabolic network is defined as a set of biochemical reactions that describes an organism metabolism, whether they are catalyzed by enzymes or not. The stoichiometric information contained in a metabolic network with m metabolites and n reactions can be represented by a stoichiometric matrix with rows and columns associated to metabolites and reactions respectively. This matrix is of crucial importance, as it represents the translation of biological knowledge into mathematical terms (Llaneras and Picó, J. Biosci. Bioeng. (2008) 105 (1):1-11).

In order to establish *Acidithiobacillus ferrooxidans* Wenelen's metabolic network, its genomic sequence, containing the information of the proteins this organism is capable of synthesizing, was considered. From *Acidithiobacillus ferrooxidans* Wenelen's genome it is possible to infer its enzymes and reconstruct the set of reactions that it can generate.

To accurately represent *Acidithiobacillus ferrooxidans* Wenelen biochemistry, it was necessary to account for the synthesis of its biomass precursor metabolites. To do this, a search for available information on its carbon central metabolism and amino acid synthesis pathways was conducted (Kim and Gadd, Bacterial physiology and metabolism, 2008). Once the main metabolic paths were established, DNA and RNA nucleic acids synthesis information was included in the network, as well as the synthesis of EPS precursors (Gehrke et al., Importance of Extracellular Polymeric Substances from *Thiobacillus ferrooxidans* for Bioleaching, Applied and Environmental Microbiology (1998) vol. 64 (7) pp. 2743-7).

The model was constructed considering 195 metabolites—13 are extracellular metabolites and 182 intracellular—and 190 reactions. Hence, a stoichiometric matrix (S) of 195 rows (m) and 190 columns (n) was obtained. The 190 reactions considered include 53 reversible reactions; 100 reactions are exclusively related to biomass constituents production; 21 reactions participate in shared processes for EPS and biomass synthesis; 44 are associated solely to EPS synthesis and 20 reactions are involved in central metabolism and energy generation.

Having defined the matrix S, the mass balance that involves each of the metabolites can be represented in mathematical terms by a set of differential equations:

$$\frac{dc}{dt} = S \cdot v - \mu \cdot c$$

where $c=(c_1, c_2, \ldots, c_m)$ is the vector of concentration of the intracellular metabolites, S is the stoichiometric matrix, $v=(v_1, v_2, \ldots, v_m)$ is the flux vector, and $\mu$ is the specific cell growth rate. This mass balance dynamic equation describes the evolution in time of the concentration of each metabolite ($c_i$).

To simplify the analysis, it is assumed that the accumulation and/or consumption of intracellular metabolites in the volume of reaction in relation to the accumulation of products and substrates consumption is negligible (pseudo stationary state assumption), obtaining the following mass balance:

$$S \cdot v = 0$$

For the stoichiometric matrix S there are m independent equations, one for each metabolite and given that the associated reactions are n, generally with n>m, the system is under-determined with (n−m) freedom degrees. Therefore, equation of mass balance defines a solution space, built by each possible flux (v) solution (Llaneras and Picó, J. Biosci. Bioeng. (2008) 105(1):1-11).

This method does not provide an unique flux distribution but it delimits the set of flux distributions which can be obtained by a metabolic network, providing a feasible space within the metabolic network can adapt depending on the substrates abundances or environmental conditions such as temperature, pH, etc. Therefore, the equation contains the metabolic capacities of the object modeled, in the present case, *A. ferrooxidans* Wenelen.

The model was programmed to perform simulations of metabolic fluxes capable to enhance EPS production in *A. ferrooxidans* Wenelen.

An analysis of model elementary modes points out that *Acidithiobacillus ferrooxidans* Wenelen is capable to canalize energy to biomass or EPS synthesis, depending of the phenotypic state of the microorganism, this is, depending on the response to environmental stimuli, *A. ferrooxidans* is capable to produce both in different proportions. Form a metabolic fluxes point of view, for a given energy consumption in *A. ferrooxidans* Wenelen, exists an inverse relation between the carbon flux used for biomass production and the one used for EPS synthesis.

Analysis of fluxes simulation results led to the conclusion that it exists one pathway which is key for biomass production but not for EPS synthesis, the tricarboxilyc acid (TCA) cycle. According to this, predictions show that if TCA cycle is blocked, carbon fluxes should be redirected towards EPS production, decreasing the biomasss production. This allows culture an inoculum of *A. ferrooxidans* Wenelen EPS enriched, which is potentially more efficient in bioleaching process in contact with mineral surfaces.

As was previously stated, TCA inhibition can be made at different branches, inhibiting particular enzymes.

Aconitase (EC 4.2.1.3) is one of the enzymes involved in this cycle, which catalyze citrate conversion to isocitrate, using cis-aconitate as intermediary. This enzyme is specifically inhibited by FIC. Therefore, a culture of *A. ferrooxidans* containing FIC will produce less biomass but this will be enriched in EPS. This also should enhance their bioleaching activity.

Example 1 shows an application of the strategy.

The application of this method using the mathematical metabolic model of *Acidithiobacillus ferroxidans*, can be used to design a culture process for *A. ferrooxidans* enriched whit EPS and therefore with enhanced properties in bioleaching.

EXAMPLE 1

To compare biomass and EPS production in a *Acidithiobacillus ferrooxidans*, a culture with FIC and a control one, without FIC, were conducted.

Both cultures were carried in 1 L of a 9K medium described in Table 2, with the addition of 30 g/L of ferrous sulfate, with pH set at 1.8, agitation of 250 rpm and air flux of 1 VVM.

Figure 2:
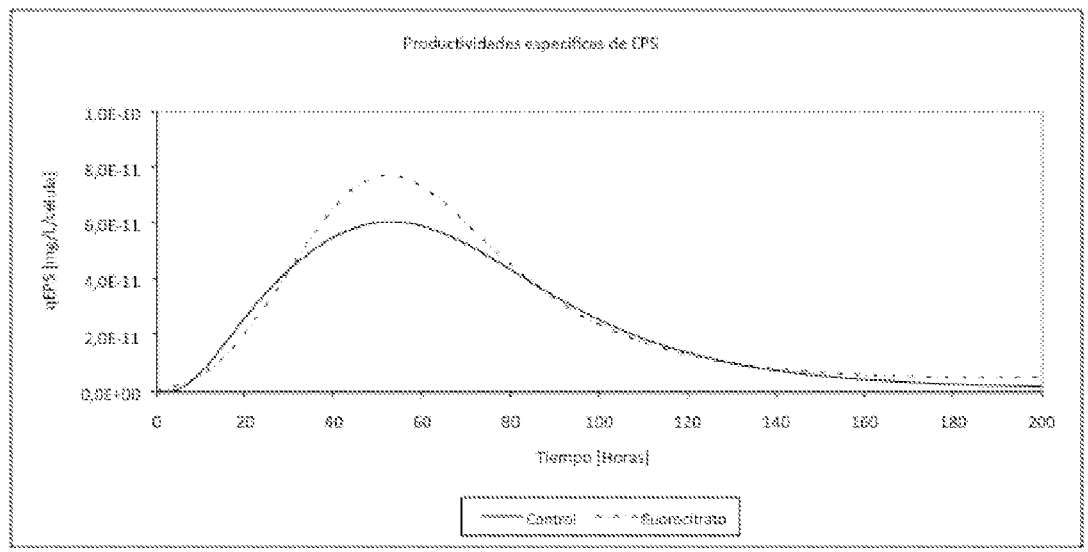
FIG. 2: *Acidithiobacillus ferrooxidans* Wenelen cultures specific productivity in control and FIC conditions according to the method of invention. After the first 30 hours, a significant increase in EPS specific productivity is observed in FIC cultures. Approximately a 30% of increase is observed around the 50 hours of culture, which is coincident with its exponential growth phase.

In both cultures, the same initial biomass concentration of $1*10^7$ cell/mL was inoculated. In sample 1, 80 µM of FIC was added. Cultures were kept for 288 hours and EPS and biomass concentration was periodically measured. Afterwards, specific productivity of EPS was calculated. Results are summarized in Tables 3 and 4 and in FIG. 2.

TABLE 2

| Liquid medium 9K | |
| --- | --- |
| Component | Concentration, (g/L) |
| $(NH_4)_2SO_4$ | 3.0 |
| $K_2HPO_4$ | 0.5 |
| $MgSO_4 \cdot 7 H_2O$ | 0.5 |
| KCl | 0.1 |
| $Ca(NO_3)_2$ | 0.01 |

TABLE 3

A. ferrooxidans strain Wenelen without additive

| Time [hours] | cel/ml | EPS mg/L | pg EPS/cel | [EPS] ajusted [mg/l] | Constants | |
|---|---|---|---|---|---|---|
| 0.0001 | 3.13E+06 | 21.8 | 6.98 | 21.80 | K | 4010157.10 |
| 24 | 8.44E+06 | 23.5 | 2.79 | 25.51 | N | 3.41 |
| 48 | 4.22E+07 | 59.75 | 1.42 | 56.99 | objetive F | 5633.82 |
| 120 | 1.11E+08 | 218 | 1.97 | 245.81 | | |
| 144 | 1.35E+08 | 317.5 | 2.35 | 274.73 | | |
| 168 | 1.62E+08 | 312.5 | 1.93 | 291.23 | | |
| 192 | 1.84E+08 | 255 | 1.39 | 300.86 | | |
| 216 | 1.38E+08 | 320 | 2.33 | 306.70 | | |
| 288 | 1.12E+08 | 297.5 | 2.67 | 314.44 | | |

TABLE 4

A. ferrooxidans strain Wenelen with 80 μM of FIC

| Time [horas] | cel/ml | EPS mg/L | pg EPS/cel | [EPS] ajusted [mg/l] | Constants | |
|---|---|---|---|---|---|---|
| 0.0001 | 4.69E+06 | 28 | 5.97 | 28.00 | K | 4010157.10 |
| 24 | 7.81E+06 | 33.5 | 4.29 | 36.49 | N | 3.67 |
| 48 | 6.66E+07 | 74 | 1.11 | 109.28 | F objetive | 7072.13 |
| 120 | 7.69E+07 | 341 | 4.44 | 306.36 | | |
| 144 | 4.16E+07 | 350 | 8.42 | 318.74 | | |
| 168 | 3.41E+07 | 372.5 | 10.94 | 324.73 | | |
| 192 | 1.41E+07 | 348.5 | 24.78 | 327.88 | | |
| 216 | 1.38E+07 | 315 | 22.91 | 329.65 | | |
| 288 | 1.94E+07 | 305 | 15.74 | 331.83 | | |

For the appropriate calibration of the model, the control sample was used. In this sample, a batch culture of *Acidithiobacillus ferrooxidans* was kept for 288 hours. Considering the data from measurements taken between 24 and 192 hours of culture (exponential growth phase period) a specific growth rate of m=0.016 h$^{-1}$ (R$^2$=0.85) was determined.

Ferric ion in the culture medium at an initial concentration of 6 g/L was completely consumed during bacterial growth (between hours 24 and 196). Then, it is possible to estimate the biomass yield over Fe$^{+2}$ (Y$_{xs}$) integrating the following equations:

$$\frac{dS}{dt} = -Y_{xs}\mu X$$

$$X(t) = X_0 e^{(\mu \cdot t)}$$

with X$_0$=1.0*10$^7$ cel/mL.

A yield of 17.8 mol of Fe$^{+2}$ per gram of biomass dry weight (DW) is then obtained.

Given that substrate flux r$_s$ can be expressed as μYxs, the estimated experimental flux is of 85,45 mM/gDWh. Yield between EPS and biomass Yxp was estimated from experimental data of 23 [g EPS]/[gDW] and the corresponding flux was of 0.35 [g EPS]/gDWh. This value is only 11% of the maximal value of [g EPS]/[gDWh]. predicted by the model. This result is consistent with published data (Gehrke et al., Importance of Extracellular Polymeric Substances from *Thiobacillus ferrooxidans* for Bioleaching, Applied and Environmental Microbiology (1998) vol. 64 (7) pp. 2743-7) given the oxidation and growth rate obtained.

In the first 48 hours there was no significant differences in the growth rate or EPS production between sample 1, with FIC, and the control sample, without FIC. Control sample EPS concentration was of 60 mg/L while in sample 1 this concentration was of 74 mg/L.

The model was used to calculate Fe$^{+2}$ consumption rate during this first stage (0-48 hours), assuming that EPS production rate in this period had to be equal to 11% of its maximal predicted value, as it was demonstrated in the model calibration experiment, and the growth rate of 0.089 h$^{-1}$. Considering this, an iron consumption rate of 121.50 mM/gDWh is obtained for this period, which is equivalent to 82% of total iron available in the system.

During the next phase, from hours 48 to 120, biomass in sample 1 remains practically constant and EPS production shows a strong increase. On the other hand, a high growth rate in the control sample continues to be observed. In this phase, EPS concentration is always higher in sample 1 in relation to the control sample, which is highly remarkable since biomass concentration in sample 1 is considerably smaller in sample 1. At 120 hours of culture, the EPS yield, expressed in pg EPS/cell, is 2 times greater in sample 1, see Table 3.

In the third phase, between 120 and 288 hours, sample 1 biomass is lower by one magnitude order that control sample, but EPS concentration in both cases are very close. The most significative difference in yield (pg EPS/cell) is achieved in 192 hours; the amount of EPS per cell is 18 times higher in sample 1 than control, as exposed in Table 3.

It is possible to appreciate clearly that predictions obtained by the model are observed in a real culture. The use of fluoroisocitrate in an *A. ferroxidans* culture, allows enhanced EPS production in detriment of biomass production, obtaining an *A. ferrooxidans* culture enriched in EPS to be used in a bioleaching system, improving efficiency of this industrial process.

Model predictions, validated by laboratory experiments, shows that an *A. ferrooxidans* incubated with FIC slows it biomass production rate and EPS is increased.

Even in low concentrations, FIC addition should increase EPS production, given the partial inactivation of aconitase.

Preferably, FIC should be added in a concentration of 10 and 200 μM; furthermore, between 70 and 120 μM.

Results show that invention application achieves significant increments in EPS productivity during exponential growth. Application of invention over a culture produces an increase for EPS productivity between 2 and 18 times, as seen in the present example.

The invention claimed is:

1. A method to enhance extracellular polymeric substances (EPS) production in an *Acidithiobacillus ferrooxidans* culture employing ferrous sulfate as a nutrient source, the method comprising inhibiting tricarboxilic acid cycle (TCA) in the *Acidithiobacillus ferrooxidans* culture by contacting the culture with fluoroisocitrate (FIC) or a salt thereof.

2. The method according to claim 1, wherein the concentration of FIC is from 10 to 200 μM.

3. The method according to claim 1, wherein the concentration of FIC is from 50 to 150 μM.

4. The method according to claim 1, wherein the concentration of FIC is from 70 to 120 μM.

* * * * *